(12) United States Patent
Yoo

(10) Patent No.: US 6,444,078 B1
(45) Date of Patent: Sep. 3, 2002

(54) MANUFACTURING METHOD FOR MOXIBUSTING IMPLEMENT OF LOESS

(76) Inventor: Tae Woo Yoo, 807, 1-Dong, Hanyang Apt., 32-5, Banpo-Dong, Seocho-Ku, Seoul (KR)

(*) Notice: Subject to any disclaimer, the term of this patent is extended or adjusted under 35 U.S.C. 154(b) by 67 days.

(21) Appl. No.: 09/739,042

(22) Filed: Dec. 18, 2000

(30) Foreign Application Priority Data

Aug. 18, 2000 (KR) .............................................. 00-47742

(51) Int. Cl.[7] .................................................. B32B 3/10
(52) U.S. Cl. ...................................... 156/256; 156/344
(58) Field of Search ............................... 428/138, 40.1; 604/24, 304, 291; 156/344, 256

(56) References Cited

U.S. PATENT DOCUMENTS

| | | |
|---|---|---|
| 5,549,960 A | 8/1996 | Yoo |
| 5,948,506 A | 9/1999 | Yoo |
| 6,083,591 A | 7/2000 | Yoo |

FOREIGN PATENT DOCUMENTS

| | | |
|---|---|---|
| KR | 9816773 | 9/1998 |
| KR | 192586 | 6/2000 |

Primary Examiner—Alexander S. Thomas
(74) Attorney, Agent, or Firm—Richard M. Goldberg

(57) ABSTRACT

A manufacturing method for a moxibusting implement of loess includes a step of attaching exfoliation papers to the upper and lower surface of a square paper board with adhesives; a step of perforating a plurality of receiving holes inside the paper board and detaching the exfoliation paper from the upper surface of the paper board; a step of attaching a filter paper to the upper surface of the paper board and cutting a plurality of shapes of holes inside the paper board; a step of applying adhesives on the upper surface of the shapes of holes; a step of attaching a plurality of loess boards on the shapes of the holes; a step of applying adhesives on the upper surface of the loess boards and attaching a plurality of moxas on the loess boards; and a step of drying the completed moxibusting implements by applying heat.

2 Claims, 4 Drawing Sheets

MANUFACTURING METHOD FOR MOXIBUSTING IMPLEMENT OF LOESS

BACKGROUND OF THE INVENTION

The present invention relates to a manufacturing method for a moxibusting implement of loess and more particularly to a manufacturing method for a plurality of moxibusting implements of loess of high quality by perforating a plurality of receiving holes, applying adhesives and attaching loess boards and moxas automatically.

In general, a traditional moxibusting implement is manufactured by adhering a supporting board comprising an upper paper board with a receiving hole, filter paper, a lower paper board and exfoliation paper in regular sequence to a loess board with a moxa attached by adhesives. The moxibusting implement was attached to a supporting board by handiwork, and therefore the manufacturing process required much time and cost. Further, there have been possibilities of inferior goods due to failing to apply adhesives on the appropriate positions exactly or limits of a production quantity because they have been made by handiwork. For example, adhesives used to be applied on only a part of the position requiring adhesives, and sometimes on even outer parts since applying adhesives were performed by handiwork.

SUMMARY OF THE INVENTION

A manufacturing method for a moxibusting implement of loess according to the invention was designed to solve the problems as described above. The object of the present invention to lessen manufacturing time required for manufacturing a plurality of moxibusting implements through an automatic manufacture.

The manufacturing method for a moxibusting implement of loess according to the present invention includes: a step of attaching exfoliation papers to the upper and lower surface of a square paper board with adhesives; a step of perforating a plurality of receiving holes inside the paper board and detaching the exfoliation paper of the upper surface of the paper board; a step of attaching a filter paper to the upper surface of the paper board and cutting a plurality of shapes of holes inside the paper board; a step of applying adhesives on the upper surface of the shapes of the holes; a step of attaching a plurality of loess boards to the shapes of the holes; a step of applying adhesives onto the upper surface of the loess boards and attaching a plurality of moxas on the loess boards; and a step of drying the completed moxibusting implements by applying heat.

Since the steps described as above are conducted in a conveyor system automatically, manufacturing time can be saved a lot comparing to traditional methods. Further, since adhesives are applied on the exact positions requiring adhesives automatically in this manufacturing system, the present invention is capable of producing a great amount of moxibusting implements of high quality at a time.

BRIEF DESCRIPTION OF THE DRAWINGS

Other objects and features of the present invention will be hereinafter explained in detail with reference to the accompanying drawings, wherein.

DESCRIPTION OF THE PREFERRED EMBODIMENTS

Figure 1:
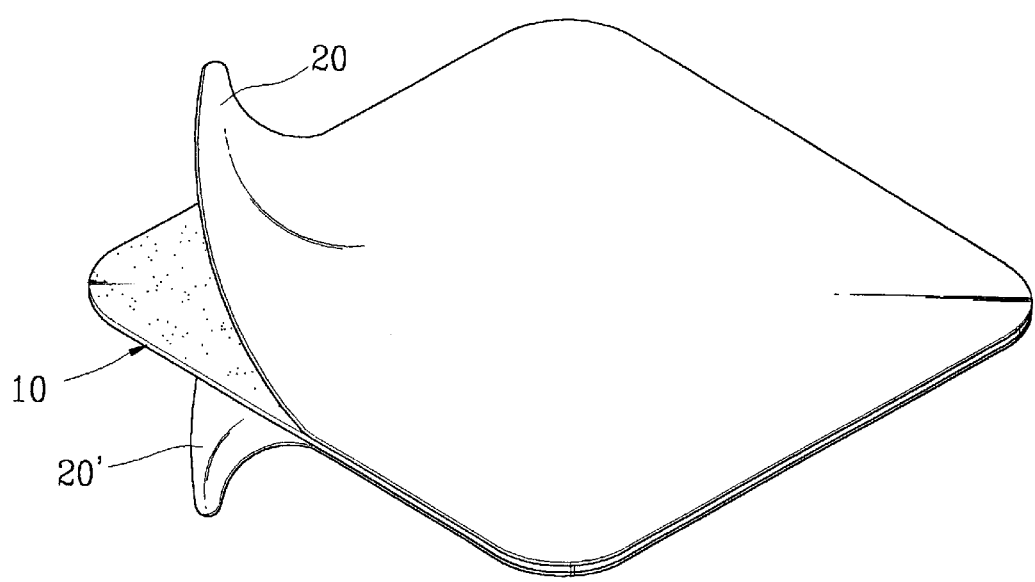
FIG. 1 is an exemplary view of a state that exfoliation papers are attached to the upper and lower surface of the paper board according to the present invention.

The manufacturing method for a moxibusting implement of loess according to the present invention is comprised of a step of attaching exfoliation papers 20, 20' to the upper and lower surface of a square paper board 10 with adhesives; a step of perforating a plurality of receiving holes 30 inside the paper board and detaching said exfoliation paper 20 from the upper surface of the paper board; a step of attaching a filter paper 40 to the upper surface of the paper board and forming a plurality of shapes of holes 50 inside the paper board; a step of applying adhesives on the upper surface of the shapes of holes; a step of attaching a plurality of loess boards 70 to the shapes of holes; a step of applying adhesives 80 on the upper surface of the loess boards 70 and attaching a plurality of moxas 90 to the loess boards; and a step of drying the completed moxibusting implements by applying heat.

More detailed description of the present invention with reference to the drawings is as follows.

Figure 2:
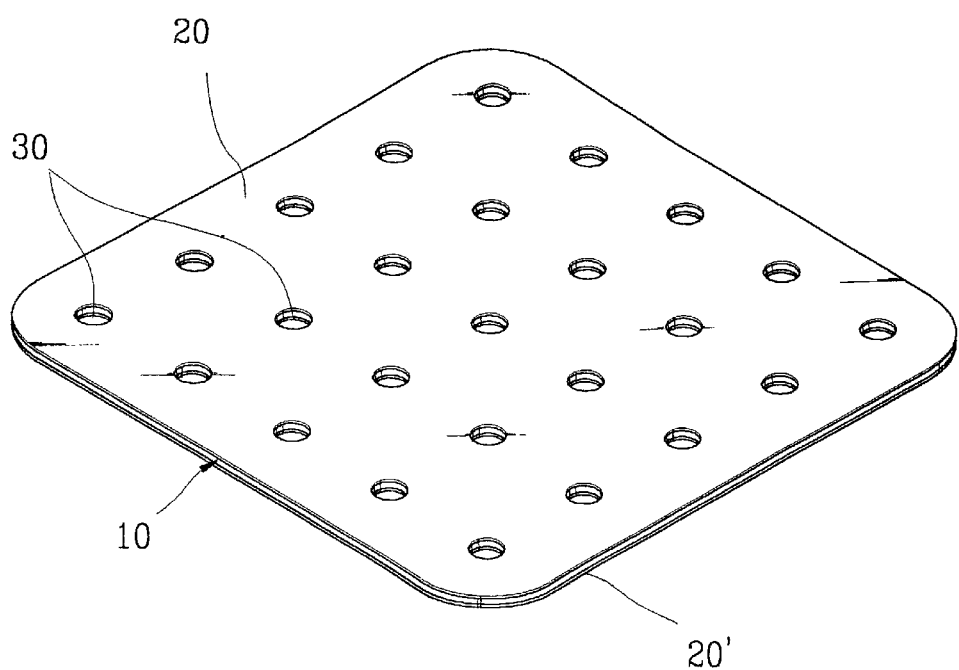
FIG. 2 is an exemplary view of a state that receiving holes are perforated on the paper board and the exfoliation paper according to the present invention.
Figure 3:
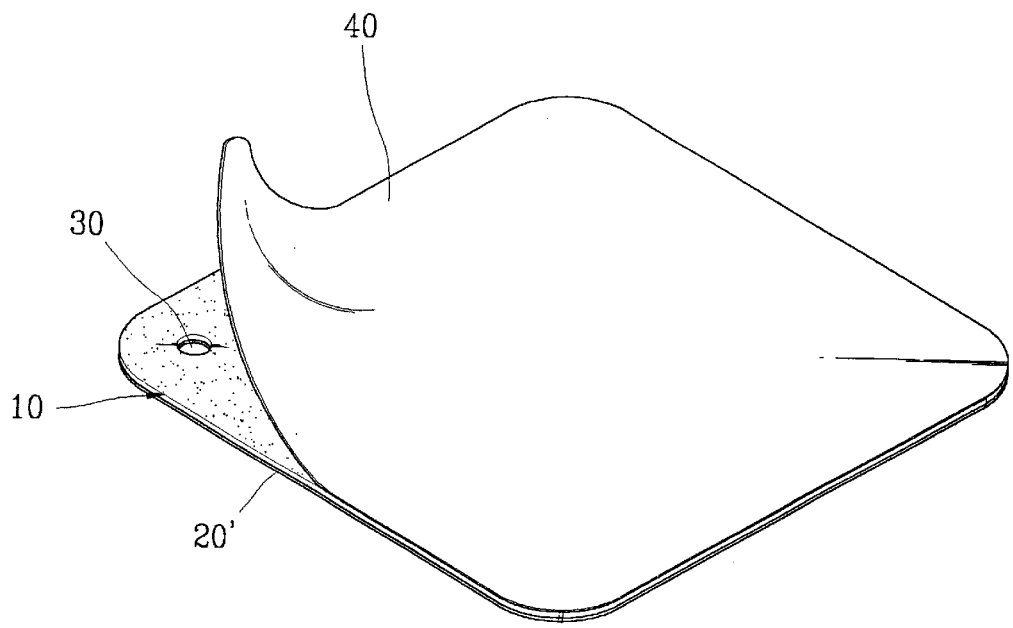
FIG. 3 is an exemplary view of the paper board from which an exfoliation paper is removed and to which a filter paper is attached.
Figure 4:
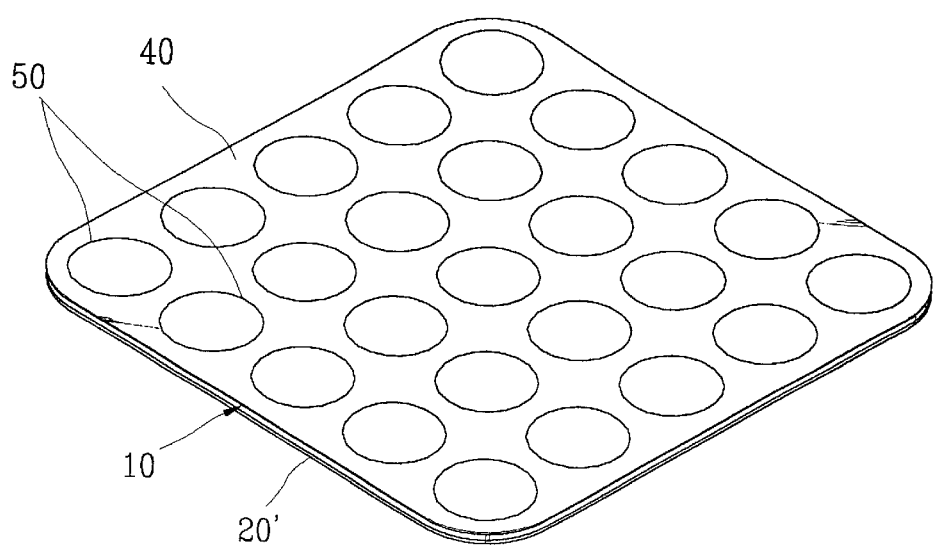
FIG. 4 is an exemplary view of the paper board where shapes of holes are perforated on the paper board according to the present invention.
Figure 5:
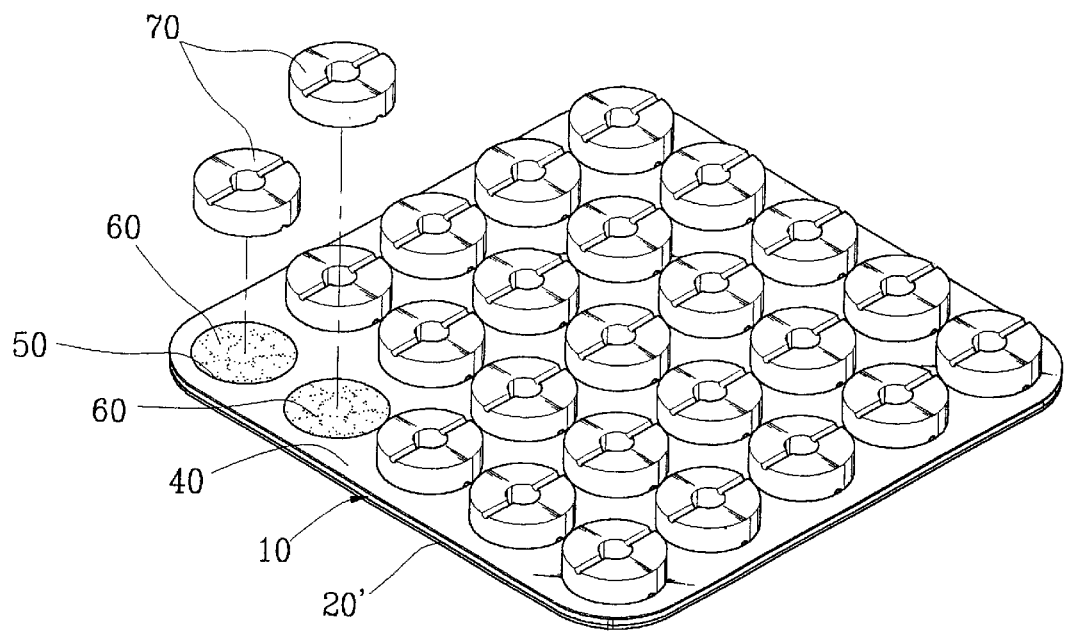
FIG. 5 is an exemplary view of applying adhesives on the shapes of the holes and attaching loess board on the shapes of holes.
Figure 6:
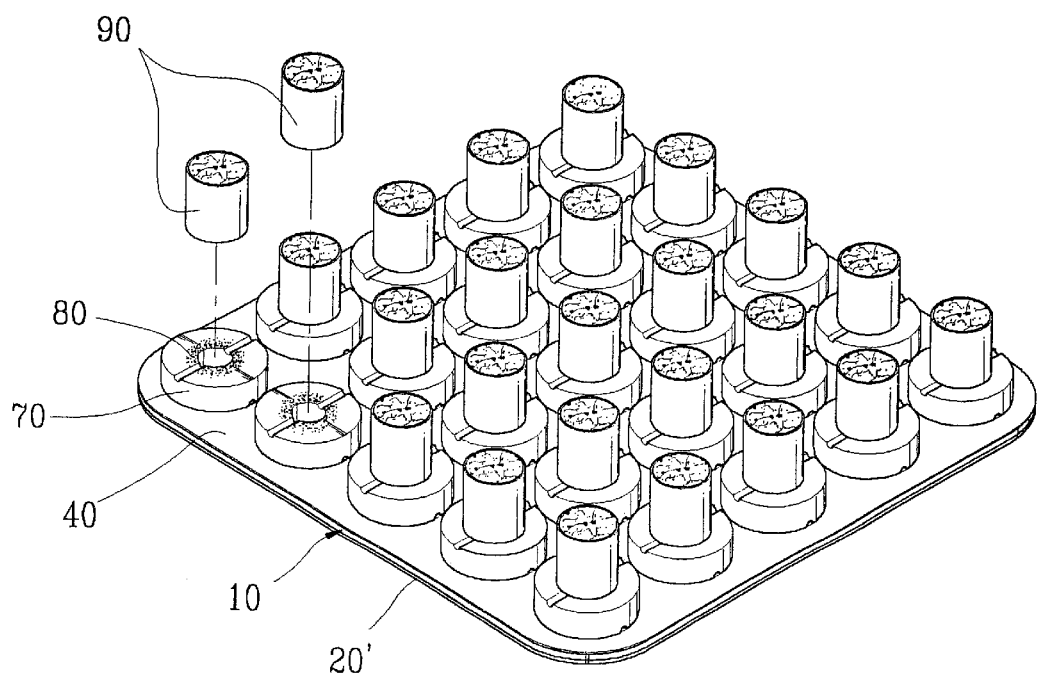
FIG. 6 is an exemplary view of applying adhesives onto the loess board and attaching moxas to the loess board.
Figure 7:
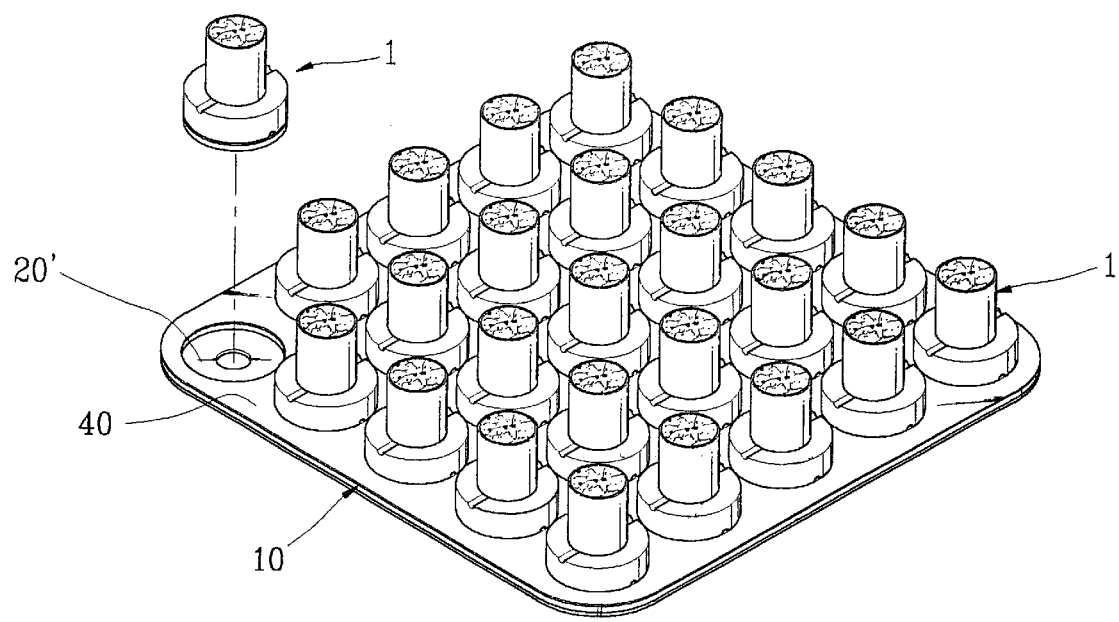
FIG. 7 is a perspective view of completed moxibusting implements.
Figure 8:
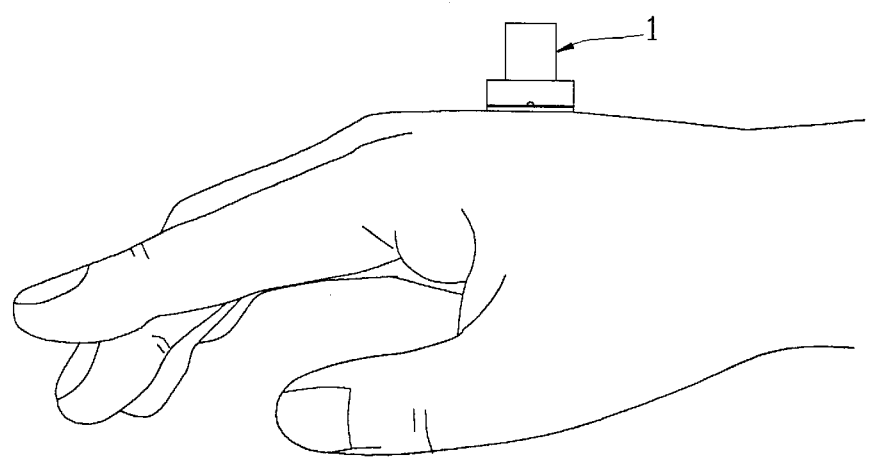
FIG. 8 is an exemplary view of performing an operation on a person.

As shown in FIG. 1, the exfoliation papers 20, 20' are attached to the upper and lower surface of a square paper board 10 with adhesives and then the paper board is sent to the next step in a conveyor (not drawn) system. As shown in FIG. 2, a perforator (not drawn) is lowered from the upper side and perforates a plurality of receiving holes 30 on the paper board with a certain distance and returns to its prior position and the paper board is sent to the next step. As shown in FIG. 3, the exfoliation paper 20 is detached from the paper board and the filter paper 40 is attached to the upper surface of the paper board and the paper board is sent to the next step. As shown in FIG. 4, the perforator is lowered from the upper side and perforates a plurality of shapes of holes 50 on the paper board and then the paper board is sent to the next step. As shown in FIG. 5, adhesives 60 from the adhesives case (not drawn) from the upper side are applied on the upper surface of the shapes 50 of holes and then the paper board is sent to the next step. At this moment, a plurality of loess boards 70 are lowered from the loess board case (not drawn) in the upper part and attached on the upper surface of the shapes 50 of holes and then the paper board is sent to the next step. As shown in FIG. 6, adhesives 80 are applied on the upper surface of the plurality of loess boards 70 and then the paper board is sent to the next step. At this moment, a plurality of moxas 90 are lowered from the moxa case (not drawn) in the upper part and attached to the upper surface of the loess boards. As shown in FIG. 7, a plurality of moxibusting implements are completed after being dried in a drying room (not drawn). As shown in FIG. 8, users detach a moxibusting implement 1 from the paper board one by one and put it on the skin after removing an exfoliation paper 20' and then ignite a moxa 90.

As described above, a plurality of moxibusting implements are produced in a conveyor system by transfers, perforations and applying adhesives in an automatic way. An automatic method of manufacturing moxibusting implements according to the present invention is capable of applying adhesives exactly on the appropriate positions on the filter paper 40 and loess boards 70 automatically. Therefore, the completed moxibusting implements have no problems relating to applying adhesives, such that adhesives are applied on only a part of the positions requiring adhesives, even on outer parts and so on.

When a user performs an operation on a person, a moxibusting implement is pulled out from the paper board and attached on the skin, after removing an exfoliation paper 20' from the paper board and the moxa is ignited. During the operation, combustion heat and warmth are penetrated into the skin through the receiving holes as shown in FIG. 8.

Further, the present invention has a strong moxibusting effect by producing far-infrared radiation heat from the loess boards and penetrating into the skin through the receiving holes.

Further, the present moxibusting implements cause no environmental pollution problems, since the moxa resin is filtered by the filter paper and completely oxidized after an operation on patients is completed. Therefore, the present invention has no possibility of causing environmental pollution problems due to perfect dissolution and oxidation after a complete combustion.

What is claimed is:

1. A method of manufacturing moxibusting implements of loess, comprising the steps of:

attaching exfoliation papers to an upper and lower surface of a paper board with adhesives;

cutting a plurality of receiving holes in said paper board and said exfoliation papers;

detaching said exfoliation paper from the upper surface of said paper board;

attaching a filter paper to the upper surface of said paper board;

perforating a plurality of hole shapes in said paper board and filter paper;

applying adhesives on the hole shapes on an upper surface of said filter paper;

attaching a plurality of loess boards on said hole shapes on the upper surface of said filter paper;

applying adhesives on an upper surface of said loess boards;

attaching a plurality of moxas on the upper surfaces of said loess boards to form completed moxibusting implements; and drying the completed moxibusting implements by applying heat.

2. A method according to claim 1, wherein said paper board has a square configuration.

* * * * *